United States Patent
Knepper et al.

(10) Patent No.: US 9,931,483 B2
(45) Date of Patent: Apr. 3, 2018

(54) DETECTION OF PERIODIC BREATHING DURING CPAP THERAPY

(71) Applicant: DeVilbiss Healthcare LLC, Somerset, PA (US)

(72) Inventors: Michael Knepper, Friedens, PA (US); Robert Joseph Thomas, Newton, MA (US); Wim Martens, Gemert (NL)

(73) Assignee: DEVILBISS HEALTCARE LLC, Somerset, PA (US)

( * ) Notice: Subject to any disclaimer, the term of this patent is extended or adjusted under 35 U.S.C. 154(b) by 844 days.

(21) Appl. No.: 14/288,792

(22) Filed: May 28, 2014

(65) Prior Publication Data

US 2015/0343161 A1    Dec. 3, 2015

(51) Int. Cl.
| | | |
|---|---|---|
| *A61M 16/00* | (2006.01) | |
| *G01F 1/00* | (2006.01) | |
| *G06F 19/00* | (2011.01) | |
| *A61B 5/087* | (2006.01) | |
| *A61B 5/00* | (2006.01) | |

(52) U.S. Cl.
CPC ......... *A61M 16/0003* (2014.02); *A61B 5/087* (2013.01); *A61B 5/4836* (2013.01); *A61B 5/7225* (2013.01); *A61B 5/7253* (2013.01); *A61M 16/0051* (2013.01); *A61M 16/0069* (2014.02); *A61M 16/026* (2017.08); *G01F 1/00* (2013.01); *G06F 19/3481* (2013.01); *A61M 2016/0027* (2013.01); *A61M 2016/0033* (2013.01); *A61M 2016/0039* (2013.01); *A61M 2205/50* (2013.01); *A61M 2205/502* (2013.01); *A61M 2230/42* (2013.01)

(58) Field of Classification Search
None
See application file for complete search history.

(56) References Cited

U.S. PATENT DOCUMENTS

| | | | | |
|---|---|---|---|---|
| 5,458,137 A | * | 10/1995 | Axe | A61F 5/56 128/204.21 |
| 5,704,345 A | * | 1/1998 | Berthon-Jones | A61B 5/087 128/204.21 |
| 5,803,066 A | * | 9/1998 | Rapoport | A61B 5/0002 128/204.21 |
| 5,831,175 A | * | 11/1998 | Fletcher-Haynes | G01F 1/667 702/100 |

(Continued)

FOREIGN PATENT DOCUMENTS

| | | |
|---|---|---|
| EP | 1259157 B1 | 6/2008 |
| EP | 2172153 A1 | 4/2010 |

(Continued)

OTHER PUBLICATIONS

Wolfowitz, J., "Estimation by the Minimum Distance Method in Nonparametric Stochastic Difference Equations.", Ann. Math. Statist. 25 (1954), No. 2, 203-217.*

(Continued)

*Primary Examiner* — (Jackie) Tan-Uyen T Ho
*Assistant Examiner* — Joseph D Boecker
(74) *Attorney, Agent, or Firm* — Carter, DeLuca, Farrell & Schmidt, LLP

(57) ABSTRACT

An improvement to a breathing therapy machine to detect and rate occurrences of periodic breathing and to alter the therapy delivered to a user of the device based on the rating.

10 Claims, 7 Drawing Sheets

(56) References Cited

U.S. PATENT DOCUMENTS

| | | | |
|---|---|---|---|
| 6,641,542 B2 | 11/2003 | Cho et al. | |
| 6,752,151 B2 | 6/2004 | Hill | |
| 6,839,581 B1* | 1/2005 | Ei-Solh | A61B 5/145 600/323 |
| 6,856,829 B2* | 2/2005 | Ohsaki | A61B 5/02416 600/310 |
| 7,070,568 B1* | 7/2006 | Koh | A61B 5/0205 600/508 |
| 7,267,122 B2 | 9/2007 | Hill | |
| 7,674,230 B2 | 3/2010 | Reisfeld | |
| 7,801,593 B2 | 9/2010 | Behbehani et al. | |
| 8,335,567 B2 | 12/2012 | Tehrani et al. | |
| 9,724,016 B1* | 8/2017 | Al-Ali | A61B 5/08 |
| 2002/0002327 A1* | 1/2002 | Grant | A61B 5/145 600/324 |
| 2002/0088465 A1* | 7/2002 | Hill | A61M 16/00 128/204.23 |
| 2003/0158466 A1* | 8/2003 | Lynn | A61B 5/00 600/300 |
| 2004/0059240 A1 | 3/2004 | Cho et al. | |
| 2004/0073098 A1* | 4/2004 | Geva | A61B 5/00 600/300 |
| 2004/0231498 A1* | 11/2004 | Li | G06F 17/30743 84/634 |
| 2005/0039745 A1* | 2/2005 | Stahmann | A61N 1/362 128/204.18 |
| 2005/0119711 A1* | 6/2005 | Cho | A61B 5/0205 607/42 |
| 2006/0070624 A1* | 4/2006 | Kane | A61M 16/00 128/204.23 |
| 2006/0084877 A1* | 4/2006 | Ujhazy | A61M 16/0051 600/483 |
| 2007/0016093 A1* | 1/2007 | Rapoport | A61B 5/0002 600/533 |
| 2007/0142741 A1* | 6/2007 | Berthon-Jones | A61B 5/087 600/534 |
| 2007/0239057 A1* | 10/2007 | Pu | A61B 5/0816 600/529 |
| 2008/0071185 A1* | 3/2008 | Beck | A61B 5/0816 600/529 |
| 2008/0177195 A1* | 7/2008 | Armitstead | A61B 5/087 600/529 |
| 2008/0251079 A1 | 10/2008 | Richey | |
| 2009/0050154 A1* | 2/2009 | Strothmann | A61M 16/00 128/204.23 |
| 2009/0131803 A1* | 5/2009 | Heneghan | A61B 5/4812 600/484 |
| 2010/0145166 A1 | 6/2010 | Pickler et al. | |
| 2010/0198588 A1* | 8/2010 | Sudo | G10L 21/038 704/205 |
| 2010/0204550 A1* | 8/2010 | Heneghan | A61B 5/0205 600/301 |
| 2010/0307500 A1* | 12/2010 | Armitstead | A61B 5/087 128/204.23 |
| 2011/0054279 A1 | 3/2011 | Reisfeld et al. | |
| 2012/0016218 A1 | 1/2012 | Lau et al. | |
| 2012/0103336 A1* | 5/2012 | Evers | A61M 16/0051 128/204.21 |
| 2012/0125337 A1* | 5/2012 | Asanoi | A61B 5/0816 128/204.23 |
| 2012/0291785 A1* | 11/2012 | Ramanan | A61M 16/0051 128/204.23 |
| 2013/0178761 A1 | 7/2013 | Adler et al. | |
| 2013/0331722 A1* | 12/2013 | Rodriguez-Villegas | A61B 5/0022 600/529 |
| 2014/0088373 A1* | 3/2014 | Phillips | A61B 5/113 600/301 |
| 2014/0142395 A1* | 5/2014 | Sattler | A61B 5/7203 600/300 |
| 2015/0038867 A1* | 2/2015 | Armitstead | A61B 5/0816 600/538 |
| 2015/0164375 A1* | 6/2015 | Schindhelm | A61B 5/08 600/534 |
| 2015/0230750 A1* | 8/2015 | McDarby | A61B 5/4812 600/407 |
| 2015/0265789 A1* | 9/2015 | Whiting | A61B 5/04 128/204.23 |
| 2016/0058964 A1* | 3/2016 | Doemer | A61M 16/0069 128/204.23 |
| 2017/0076045 A1* | 3/2017 | Landesberg | G06F 19/3431 |

FOREIGN PATENT DOCUMENTS

| | | |
|---|---|---|
| JP | 2017522059 A1 | 8/2017 |
| WO | 2013110136 A1 | 8/2013 |
| WO | 2013177621 A1 | 12/2013 |
| WO | 2015183603 A1 | 12/2015 |

OTHER PUBLICATIONS

Detection Algorithm Using Adaptive Thresholding for Identification of Normal and Cheyne-Stokes Breathing, Anusha, et al., Proc. Sec. Int'l. Conf on Advances in Computing, Control and Communication, 2012.

Anusha, A.R., et al., Detection Algorithym Using Adaptive Thresholding for Identification of Normal and Cheyne—Stokes Breathing, Proc. of the Second International Conf. on Advances in Computing, Control and Communication, Dept. of Biomedical Eng., College of Eng., 2012.

* cited by examiner

DETECTION OF PERIODIC BREATHING DURING CPAP THERAPY

FIELD OF THE INVENTION

This invention relates generally to the field of breathing therapy machines of the type used to treat obstructive and/or central sleep disorders and specifically to the treatment of such sleep disorders when periodic breathing patterns are detected.

BACKGROUND OF THE INVENTION

The term "periodic breathing" describes a respiratory pattern in which clusters of breaths exhibit a waxing and waning of the amplitude of the tidal volume of ventilation in a cyclic pattern, typically with a period of one minute or less, causing the subject to oscillate between hyperpnea and hypopnea with a crescendo-decrescendo pattern. Cyclic patterns with periods greater than one minute typically indicate a high likelihood of impaired cardiac systolic or diastolic function. In a more extreme version the clusters of breaths may be separated by periods of apnea, instead of hypopnea. Frequently the hypopneic or apneic episodes of periodic breathing contain both obstructive and central events.

Although the exact cause of periodic breathing in adults has not been firmly established, it is thought that the cause may be related to excessive loop gain in the feedback control involved in the regulation of respiratory drive. In adults, periodic breathing is considered abnormal, and is often associated with subjects having neurologic dysfunction or heart failure.

During CPAP therapy, detection of periodic breathing is crucial, as it may be desirable to alter the therapy delivered to the subject if periodic breathing is present. For example, a normal reaction to the detection of an obstructive apnea may be to gradually raise the pressure delivered to the subject until the apneas are eliminated or converted to hypopneas. However, this rise in pressure can actually aggravate a periodic breathing respiratory pattern. Thus, it may be desirable to alter the treatment delivered by the device when periodic breathing is detected.

Current prior art devices are somewhat adept in detecting periodic breathing, but they lack sensitivity and the ability to distinguish between mild periodic breathing and severe periodic breathing. Therefore, it would be desirable to be able to detect periodic breathing with more sensitivity and to be able to distinguish between mild and severe periodic breathing such that delivered therapy may be adjusted accordingly.

SUMMARY OF THE INVENTION

Detecting periodic breathing in a subject using a breathing therapy device is useful to ensure proper pressure therapy is administered to the subject, and to determine the ongoing suitability of breathing therapy for the subject. Periodic breathing exists in a range of patterns from obvious, almost mechanical rhythmic patterns to more visually obscure and less self-similar patterns which are nevertheless still biologically significant for the subject. The goal of the present invention is to detect periodic breathing with a sensitivity that detects a broad range of periodic breathing, from less obvious marginal periodic breathing to the obvious 'text book' periodic breathing, and to categorize the periodic breathing in multiple classes of severity, which is also useful in determining the overall severity of the subject's propensity to exhibit this pattern.

The method of the present invention uses numerous signal processing techniques to detect periodic breathing patterns. Hilbert transforms are used to calculate analytical representations of a plurality of breathing measures. Ranking filters are used to remove "momentary" discontinuities in the periodic breathing crescendo/decrescendo signal, which allows periodic breathing detection to span across discontinuities in phase due to arousals. The method also grades the severity of the detected periodic breathing (none, mild, moderate, severe).

The result is a method of detecting periodic breathing which is more sensitive than existing prior art methods. In addition, an apparatus consisting of a breathing therapy device implementing the method is also presented, which is capable of altering the therapy strategy based on the rated severity of the detected periodic breathing.

DETAILED DESCRIPTION OF THE INVENTION

Figure 6:
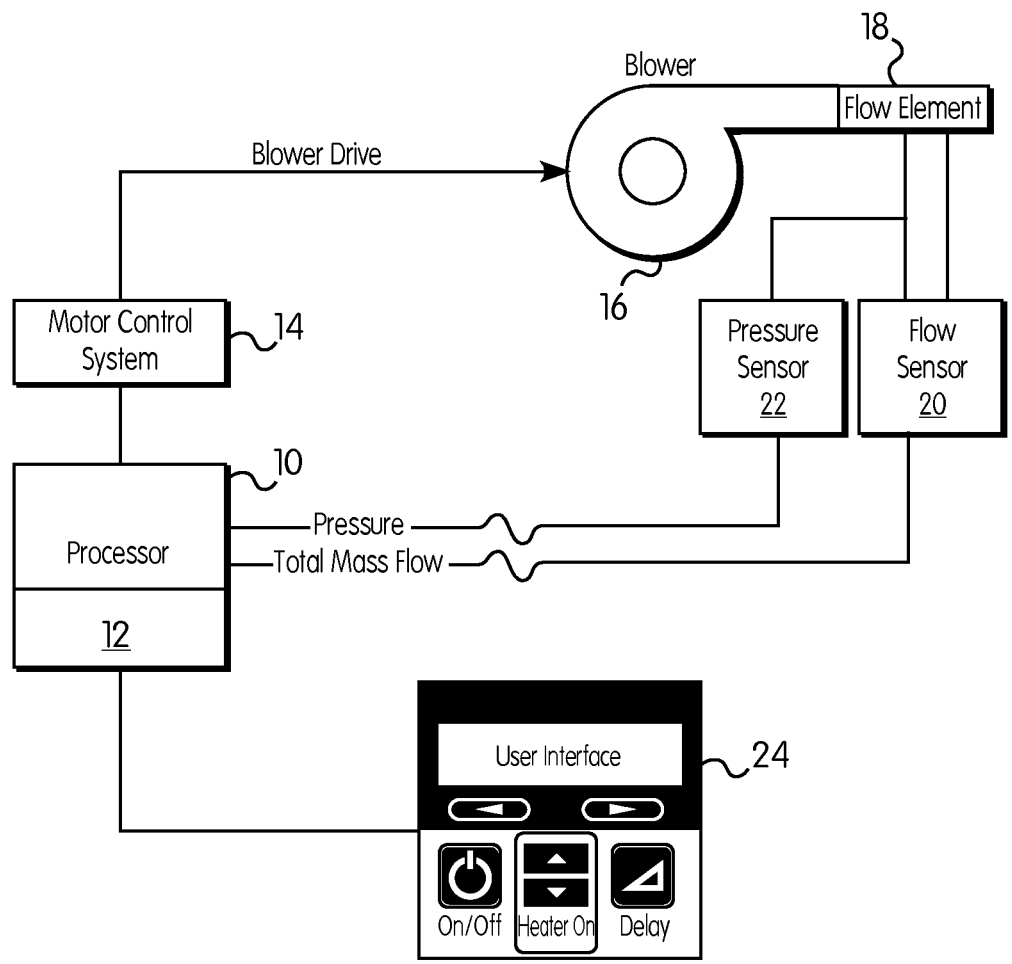
FIG. 6 is a block diagram of a breathing therapy machine of the type in which the method of the present invention would be implemented.

The method of the present invention would typically be implemented as firmware in a breathing therapy device, such as a CPAP or Bi-PAP machine of the type shown in FIG. 6. Referring now to FIG. 6, there is shown a typical breathing gas delivery system. The breathing gas delivery system comprises a processor 10 having control software/firmware 12 stored in local memory. Motor control system 14 controls the speed of blower 16 under the control of processor 10. Flow element 18 is connected to a patient interface (not shown) for the delivery of pressurized airflow. Mass flow sensor 20 senses the total flow (tidal volume) through flow element 18, and pressure sensor 22 detects the system pressure. Both flow sensor 20 and pressure sensor 22 interface with processor 10 to provide feedback regarding the patient's breathing patterns. Using interface 24 allows a patient and/or therapist to control the device.

The method of detecting periodic breathing will be described in reference to FIGS. 2-5. Now with reference to FIG. 2, in Step 1 of the process, in box 101, raw total flow rate data from flow sensor 20 is sampled and A/C coupled. A Butterworth 2nd order, high-pass filter is applied to remove residual DC, which may be present due to bias flow and leakage, and which would interfere with subsequent signal processing steps. This results in a signal representing the patient flow data sampled at 250 Hz and labeled "A" on FIG. 2. An exemplary wave form of patient flow data can be FIG. 7, Reference "A".

Figure 1A:
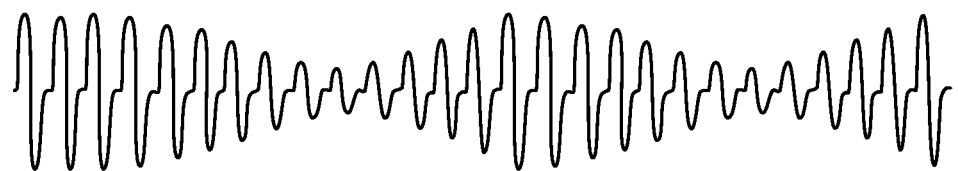
FIG. 1a shows an example of generalized periodic breathing.
Figure 1B:
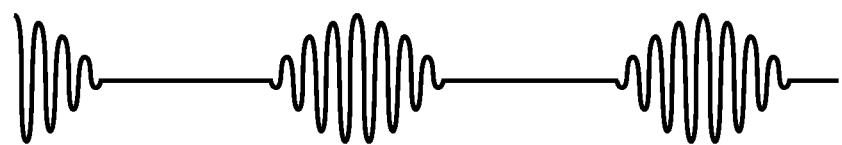
FIG. 1b shows an example of periodic breathing which would be classified as Cheyne-Stokes respiration.
Figure 2:
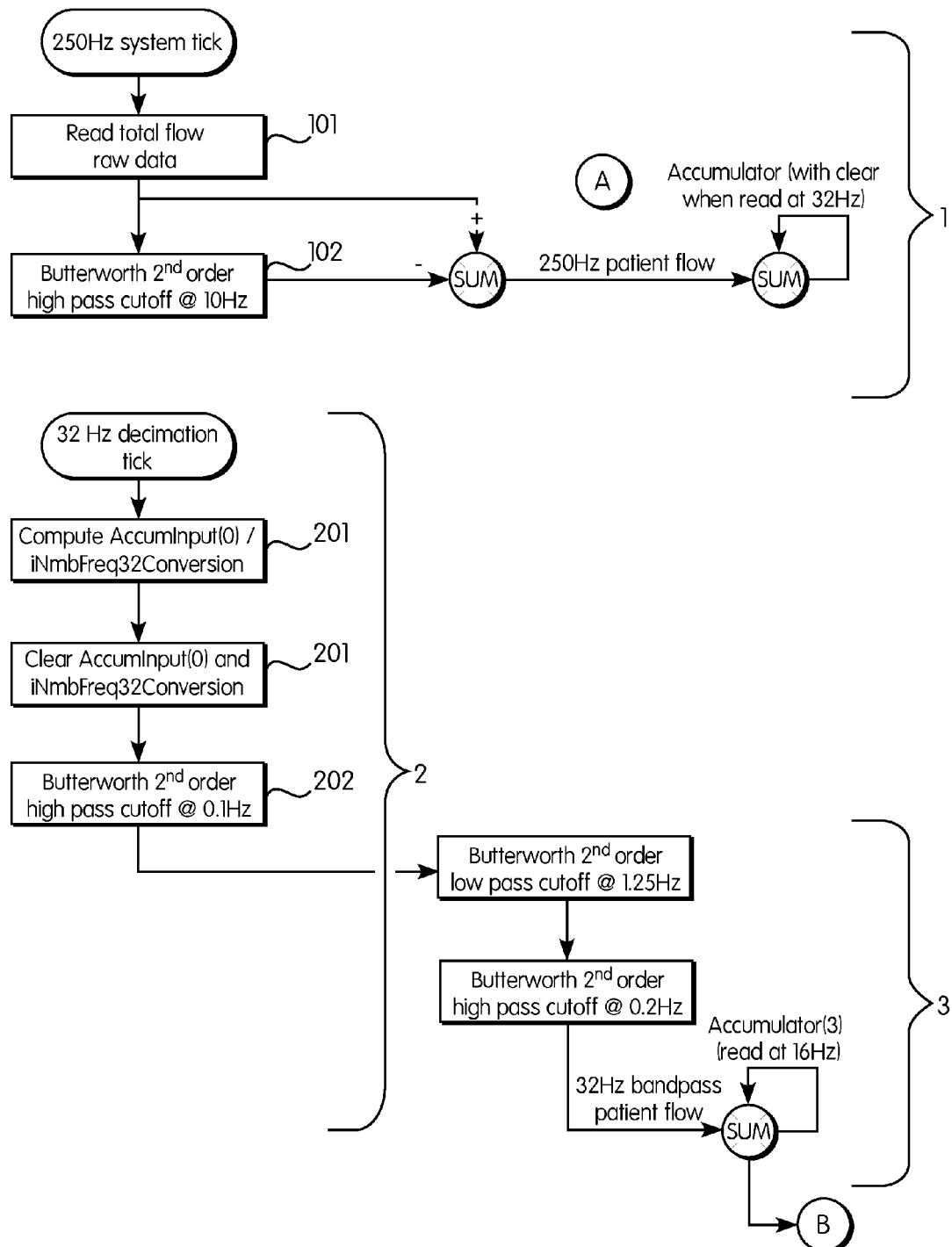
FIGS. 2-5 show a flow chart of the method of the present invention.

In Step 2 of the process in FIG. 2, the patient flow signal is decimated or down-sampled to create a waveform more suitable for analytical processing. For example, the 250 Hz waveform may be down sampled at 32 Hz. At box 201, the data is sampled at the lower rate and at box 202, an additional high-pass filter is applied to filter out any additional DC that may be present.

In Step 3 of the process in FIG. 2, the breathing signal is again down-sampled and filtered via a two point accumulator filter and a Butterworth 2nd order band pass filter is applied at boxes 301 with normal respiration upper and lower limit rates. In a preferred embodiment of the invention, the low-pass filter has a cut-off frequency of 1.25 Hz and the high-pass filter has a cut-off frequency of 0.2 Hz. This results in signal B, which is fed into Step 4 of the process, shown in FIG. 3.

Figure 3:
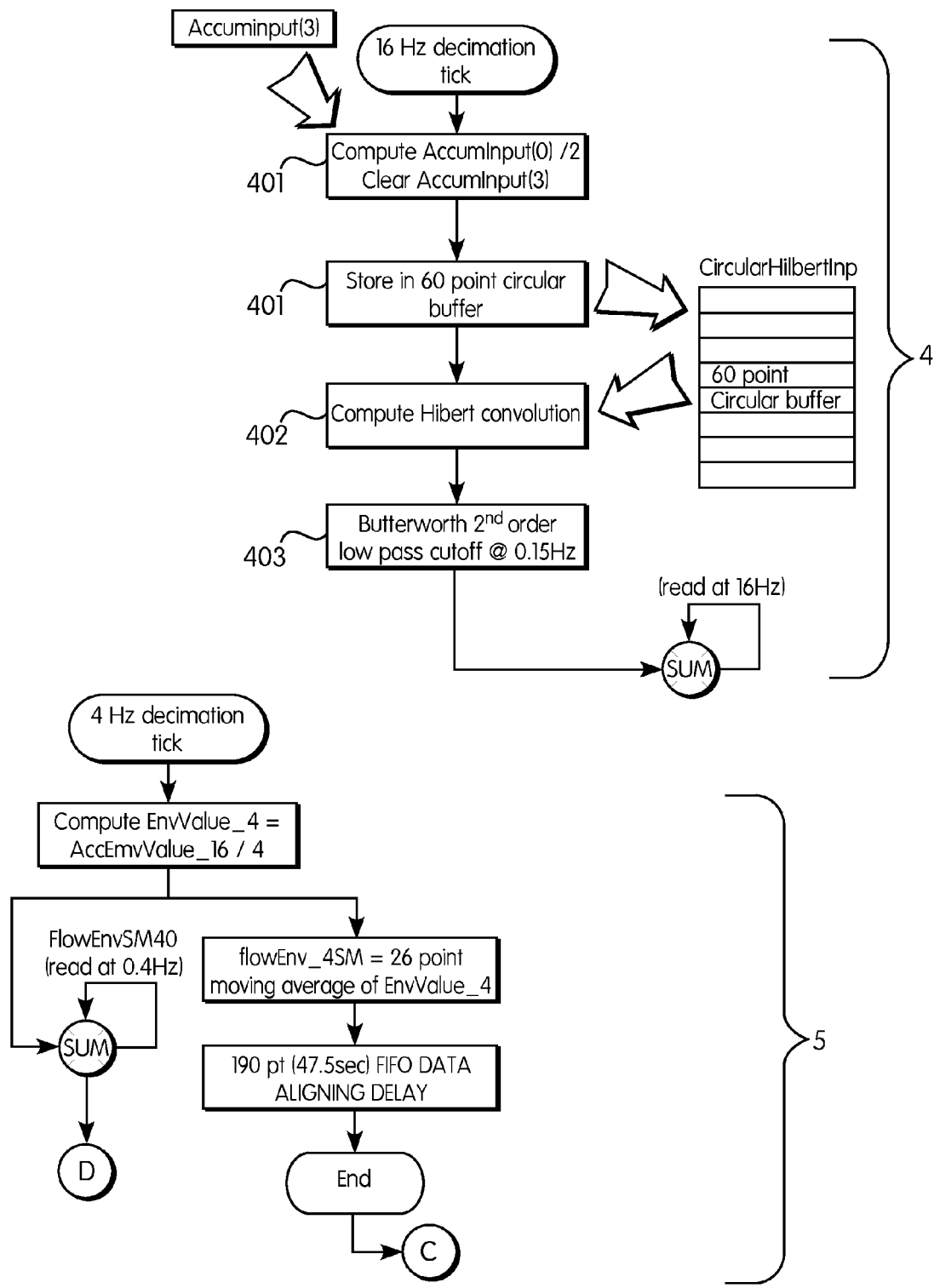

In Step 4 of the process, shown in FIG. 3, the true respiration is computed utilizing signal B as the input. Signal B is down sampled at 16 Hz in box 401 and the Hilbert Transformation is applied in box 402. 2 The Hilbert Transformation applied in box 402 produces the envelope of respiration and represents the power of the respiration itself. This signal represents a continuous tidal volume. Further filtering is applied in box 403, resulting in a signal that represents the true respiration power, which is used as input to Step 5 of the process.

Figure 7:
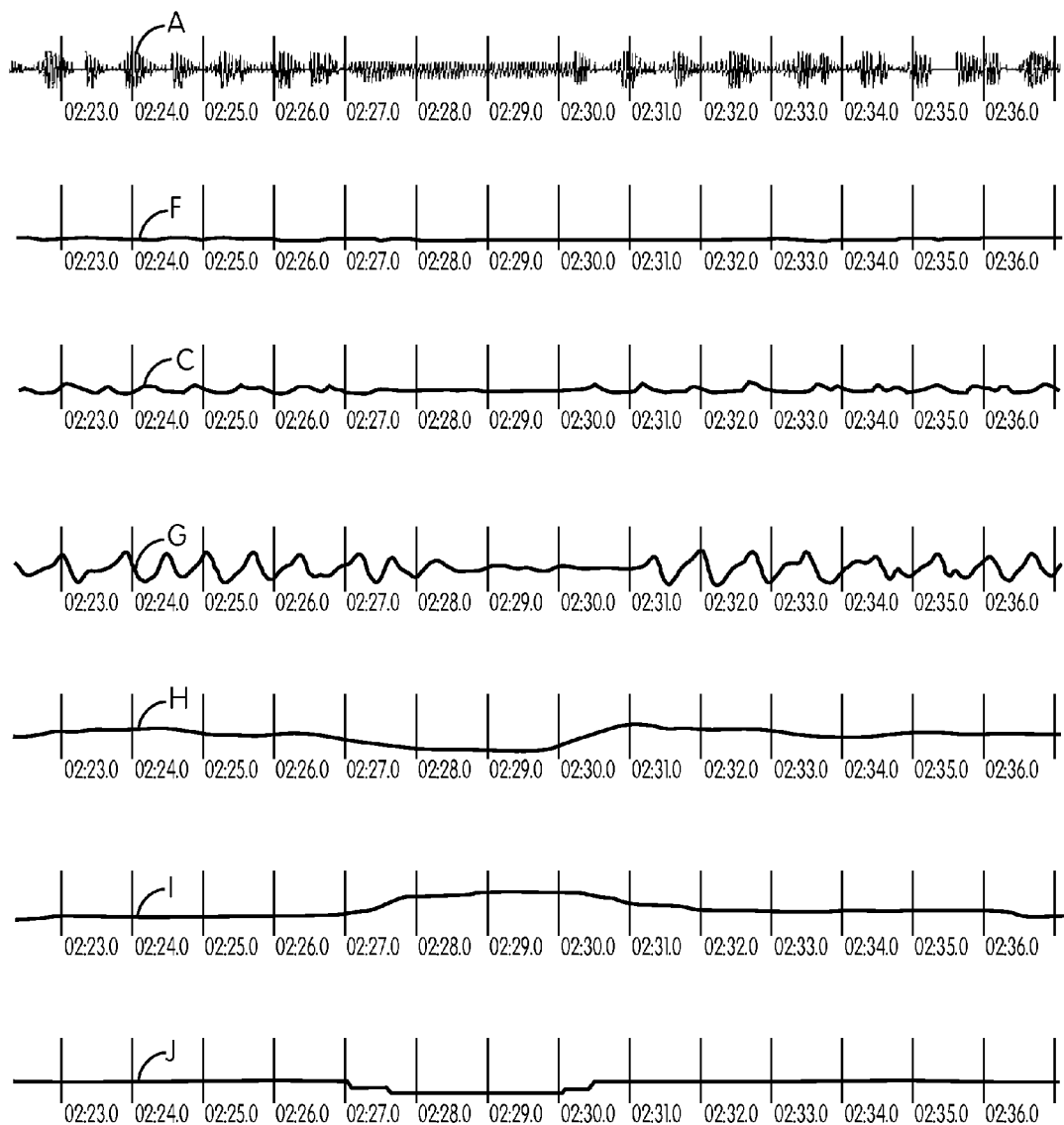
FIG. 7 shows various intermediate waveforms generated by the method of the present invention.

In Step 5 of the process, also shown in FIG. 3, the respiration power signal is again down-sampled using a four point accumulator, and the respiration power envelope is computed via a 7.5 second moving average. An example of this signal, labeled "C" in FIG. 3, is shown in FIG. 7 as Reference C, and represents a true measure of respiration (in L/Min). Signal "D" is also produced in Step 5 of the process and is used as an input for Step 6.

Figure 4:
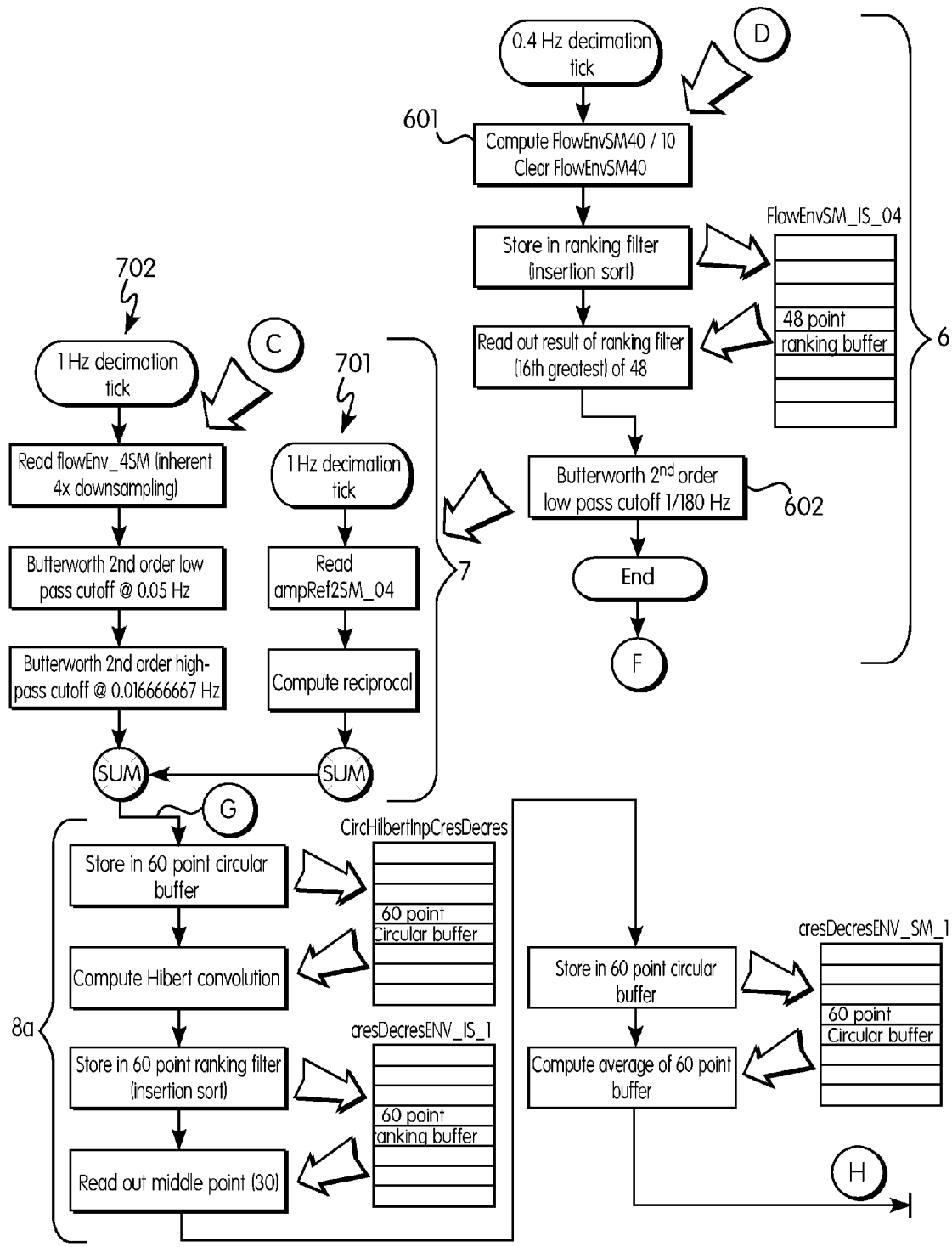

In Step 6 of the process, shown in FIG. 4, signal "D" is used to create a second respiration power signal to be used as a long-term respiration reference signal. The signal is again down-sampled at box 601 and filtered at box 602. The result is shown as signal "F" in FIG. 4 and a example if this signal is shown in FIG. 7 as Reference "F".

In Step 7 of the process, through a series of ranking filters and further band-pass filtering in the range of expected cyclic waning and waxing cycles, a ratio of a fast moving average vs. a slow moving average is computed resulting in a signal with normalized amplitude (and therefore adaptive to amplitude) representing waxing/waning cycles of periodic breathing. Referring to Step 7 on FIG. 4, the small moving average is calculated by boxes 701 and takes as input Signal "F" from Step 6. The fast moving average is computed by boxes 702 using Signal C produced by Step 5 of the process. The ratio is calculated at box 703 and represents the normalized amplitude Signal "G", which is utilized as an input to Step 8a and an example of which is shown in FIG. 7 as Reference "G". This signal represents the crescendo and decrescendo pattern of the patient flow signal A as a sine-like waveform. The presence of the sine-like waveform represents periods of periodic breathing. It can be seen in FIG. 7 that the sine-like waveform goes away during the period of normal breathing shown in Signal "A".

In Step 8a, also shown on FIG. 4, the true waxing and waning power is computed as the envelope of the normalized amplitude Signal "G" via the application of a Hilbert Transform in box 801. This signal is shown as Signal "H" in FIG. 4 and an example of this signal is shown in FIG. 7 as Reference "H". Signal "H" is used as an input to Step 9 of the process to compute the severity of the periodic breathing. It should be noted that the higher the value of this signal, the higher the severity of the periodic breathing.

Figure 5:
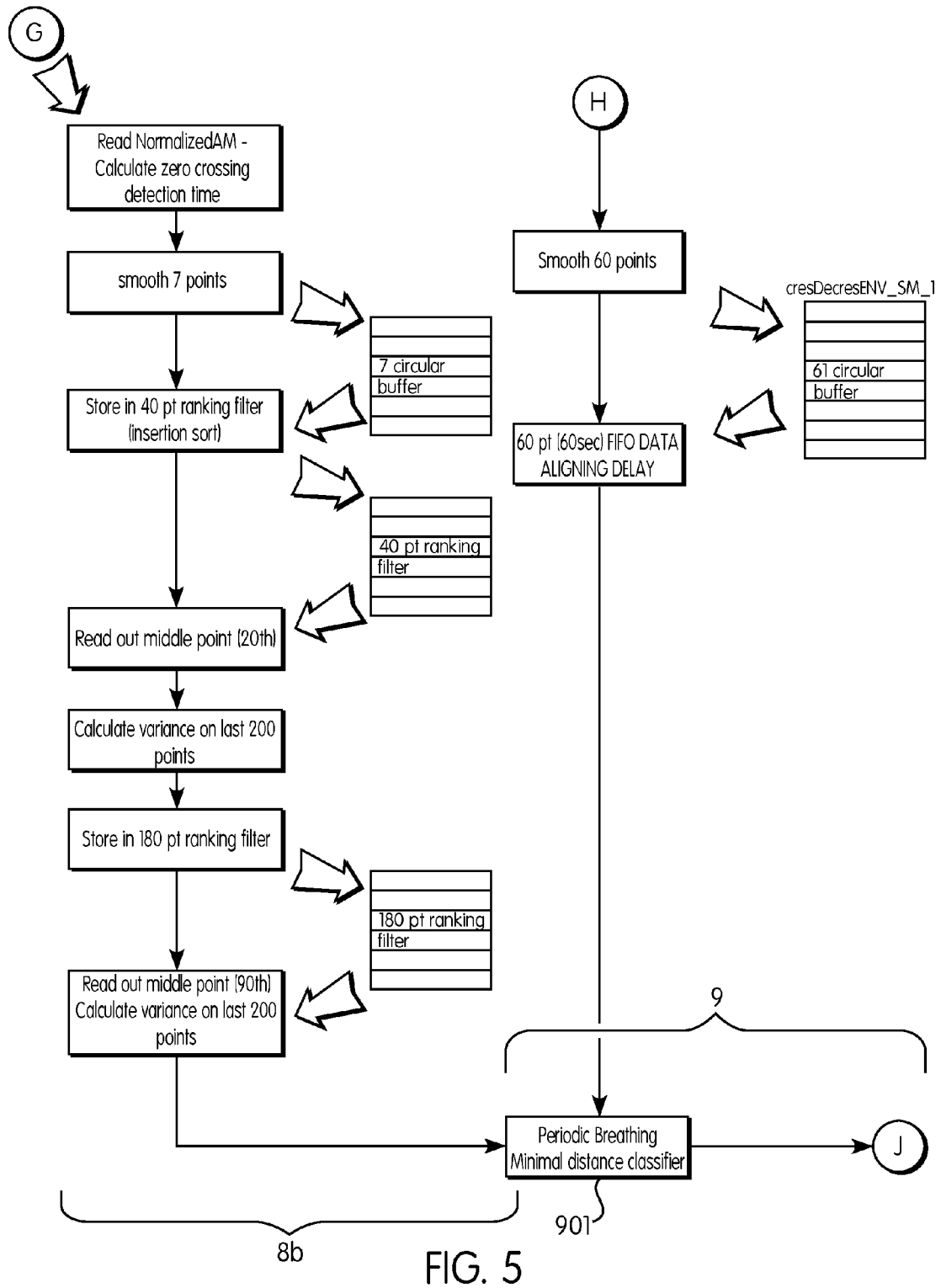

In Step 8b of the process, also shown in FIG. 5, a moving cyclic variance calculation is performed on the normalized amplitude to Signal "G" to create an analytical representation of cyclic regularity. This is shown as Signal "I" in FIG. 7 and represents the variance in the zero crossings between the sign-like waveform of Signal "G" and a true sine waveform. In general, the lower this number, the more regular the periodic breathing.

In Step 9 of the process, also shown in FIG. 5, the two input signals, namely the crescendo-decrescendo envelope Signal "H" and the crescendo-decrescendo zero crossing variance Signal "I" are input to a minimal distance statistical classification technique that classifies the inputs with four degrees of periodic breathing. (i.e., none, mild, moderate and severe). The final output signal of the process is shown as Signal "J" in FIG. 7. In this particular case, during the periods of patient flow data shown as Signal "A" in FIG. 7, the algorithm has rated the periodic breathing as moderate, while the regular breathing is noted as having no periodic breathing component.

The calculation of the rating of the severity of the periodic breathing used as Signal "H" (the crescendo-decrescendo envelope) and Signal "I" (the crescendo-decrescendo zero crossing variance) as inputs. For each of these signals, a band of values is defined representing each of the four categories of the severity of periodic breathing. The membership of each data point from Signals H and I are analyzed using a minimal distance estimation technique, which is a statistical method for fitting a mathematical model to empirical data. The algorithm may be tweaked by changing the values that define the bands for Signals H and I. In general, the larger the value for the crescendo-decrescendo envelope (Signal H) and the lower the crescendo-decrescendo zero crossing variance (Signal I), the more severe and/or the more likelihood of period breathing being present.

The Applicants note that the algorithm presented is optimized for one minute cycles. However, this can be easily changed by varying the parameters of the filtering which is applied to the signals. Also note that in the preferred embodiment of the invention, Butterworth 2nd order filters are used throughout, however, any other type of filter producing a suitable result may be used. In addition, the cutoff values for the filters have been selected to capture the vast majority of periodic breathing scenarios.

Also, as part of this invention, as implemented in a breathing therapy machine, the therapy pressure may be varied based upon the detection of periodic breathing. For example, if periodic breathing is determined to be mild and respiratory events are detected, then the machine may not respond to the respiratory events by increasing pressure. Therefore, when obstructive apnea, for example is detected, when it is time to make a pressure change decision, if periodic breathing is also present, no increases in pressure may be implemented. In the event that the periodic breathing transitions to moderate or severe, if it stays there for a minimum period of time, then the therapy pressure may be dropped. As it is known that increased pressure may aggravate periodic breathing. The actual method of altering the therapy pressure based upon the presence or lack thereof of periodic breathing may be tweaked based upon desired outcomes. However, the decision to change or not change the therapy pressure utilizes the presence or lack thereof of the periodic breathing as an input to that decision.

Although a specific embodiment of the process has been described herein, it should be realized by one of skill in the art that many implementations are possible which would fall within the scope of the invention, which is represented by the following claims.

We claim:

1. A breathing therapy device comprising:
    a blower;
    a processor;
    a flow sensing element, for sensing total flow of air and said processor configured to:
        collect flow data from said flow sensing element;
        analyze said flow data to detect patterns of periodic breathing in a user of said device;

rate the severity of said periodic breathing, wherein rating the severity of said periodic breathing comprises configuring said processor to:
  calculate a power envelope of a normalized amplitude signal representing waxing and waning cycles of said patient flow data;
  calculate a signal representing a zero crossing variance of said normalized amplitude signal; and
  classify the severity of said periodic breathing using said power envelope of said normalized amplitude signal and said signal representing the zero crossing variance; and
alter therapy delivered to said user based on said rated severity of said periodic breathing.

2. The breathing therapy device of claim 1 wherein said normalized amplitude signal is
  a ratio of a fast moving average and a slow moving average of a power envelope of a patient flow signal derived from said flow data.

3. The breathing therapy device of claim 2 wherein said power envelope of said patient flow signal and said power envelope of said normalized amplitude are calculated using Hilbert Transforms.

4. The breathing therapy device of claim 2 wherein in order to derive said patient flow signal from said flow data said processor is further configured to:
  down sample said flow data received from said flow sensing element; and
  apply a high pass filter to filter out a DC component of said flow data, representing bias flow.

5. The breathing therapy device of claim 4 wherein said high pass filter is a 2nd order Butterworth filter.

6. The breathing therapy device of claim 2 wherein, in order to rate the severity of said periodic breathing, said processor is further configured to:
  define ranges for said power envelope of said normalized amplitude signal and for said signal representing the zero crossing variance of said normalized amplitude signal for each category of severity;
  calculate said rating as a function of time based on a membership of said power envelope of said normalized amplitude signal and said signal representing the zero crossing variance of said normalized amplitude signal in each of said categories.

7. The breathing therapy device of claim 6 wherein said membership in said categories is calculated using a statistical analysis.

8. The breathing therapy device of claim 7 wherein said statistical analysis utilizes a minimum distance estimation algorithm.

9. The breathing therapy device of claim 2 wherein altering therapy delivered to said user includes ceasing an increase in pressure when apnea events are detected.

10. The breathing therapy device of claim 2 wherein altering therapy delivered to said user includes decreasing pressure when sustained periods of periodic breathing are detected.

* * * * *